(12) United States Patent
Sugiyama et al.

(10) Patent No.: US 7,824,531 B2
(45) Date of Patent: Nov. 2, 2010

(54) MULTILAYERED AIR-FUEL RATIO SENSOR

(75) Inventors: Tomio Sugiyama, Nagoya (JP); Hiromi Sano, Nagoya (JP); Masahiro Shibata, Nagoya (JP); Midori Shibata, legal representative, Nagoya (JP); Natsumi Shibata, legal representative, Nagoya (JP); Raina Shibata, legal representative, Nagoya (JP); Syuichi Nakano, Kariya (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/098,730

(22) Filed: Jun. 18, 1998

(65) Prior Publication Data
US 2001/0047937 A1     Dec. 6, 2001

(30) Foreign Application Priority Data
Jun. 19, 1997   (JP) .................................. 9-180735

(51) Int. Cl.
*G01N 27/406*     (2006.01)
(52) U.S. Cl. ....................... 204/426; 204/425
(58) Field of Classification Search ................. 204/421, 204/424–429
See application file for complete search history.

(56) References Cited

U.S. PATENT DOCUMENTS

| | | | | |
|---|---|---|---|---|
| 3,935,089 | A | * | 1/1976 | Togawa et al. ............... 204/429 |
| 4,177,112 | A | * | 12/1979 | Suzuki et al. ................ 204/429 |
| 4,559,126 | A | * | 12/1985 | Mase et al. ................... 204/425 |
| 4,722,779 | A | | 2/1988 | Yamada et al. |
| 4,755,274 | A | * | 7/1988 | Mase et al. ................... 204/425 |
| 4,765,880 | A | | 8/1988 | Hayakawa et al. |
| 4,861,456 | A | * | 8/1989 | Mase et al. ................... 204/426 |
| 5,110,442 | A | | 5/1992 | Kojima et al. |
| 5,169,513 | A | * | 12/1992 | Mase et al. ................... 204/425 |
| 5,288,389 | A | | 2/1994 | Yamada et al. |

FOREIGN PATENT DOCUMENTS

| | | |
|---|---|---|
| DE | 3632456 | 4/1987 |
| DE | 3703707 | 8/1987 |
| DE | 3910272 | 10/1989 |
| EP | 0 422 665 | 4/1991 |
| JP | 61-14187 | 1/1986 |
| JP | 61-51557 | 3/1986 |
| JP | 1-91253 | 6/1989 |
| JP | 2-62955 | 3/1990 |
| JP | 02-091557 | 3/1990 |
| JP | 03-165253 | 7/1991 |

(Continued)

OTHER PUBLICATIONS

Sumitomo Chemical Co., Ltd., "High Purity/Fine Alumina".

(Continued)

*Primary Examiner*—Kaj K Olsen
(74) *Attorney, Agent, or Firm*—Nixon & Vanderhye PC (57) ABSTRACT

A multilayered air-fuel ratio sensor consists of a plurality of substrate layers. At least one heterogeneous boundary layer is interposed between the plurality of substrate layers. The heterogeneous boundary layer has a thickness in a range of 10 to 100 μm. The heterogeneous boundary layer absorbs thermal shocks or any other stresses acting on the substrate layers and stops the growth of cracks.

31 Claims, 9 Drawing Sheets

FOREIGN PATENT DOCUMENTS

JP          04-166757          6/1992

OTHER PUBLICATIONS

Hamano et al; Journal of the Ceramic Society of Japan; Some Properties and Sinterability of High Purity Alumina Fine Powders (in Japanese); vol. 94 No. 3; 1986.

Yokota et al; Journal of the Ceramic Society of Japan; Effects of Ground Alumina Powder on Platelike Grain Growth (in Japanese); vol. 106, Feb. 1998.

English translation of published Article "High-Purity/Fine Alumina"; Sumitomo Chemical Co., Ltd.; 3 pages.

English translation of published Article; Mohri et al; Development of Advanced Alumina "Sumicorundum"; 26 pages.

Japanese Official Action dated Jun. 29, 2006 issued in corresponding Japanese Appln. No. H09-180735 with English translation.

German Official Action dated Sep. 4, 2008, issued in counterpart German Application No. 19827253.7-52 with English translation.

* cited by examiner

HETEROGENEOUS LAYER'S THICKNESS

MULTILAYERED AIR-FUEL RATIO SENSOR

BACKGROUND OF THE INVENTION

The present invention relates to a multilayered air-fuel ratio sensor used for controlling an air-fuel ratio of a gas mixture supplied to a combustion chamber of an internal combustion engine.

To suppress energy loss (i.e., fuel loss) and prevent serious air pollution, using an air-fuel ratio sensor is inevitably required for present passenger vehicles.

Figure 13:
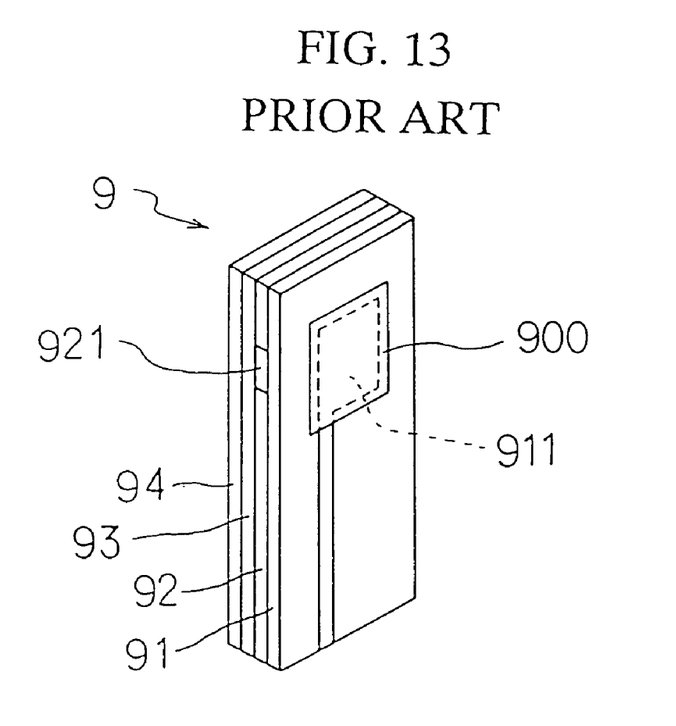
FIG. 13 is a perspective view showing an overall arrangement of a conventional multilayered air-fuel ratio sensor.
Figure 14:
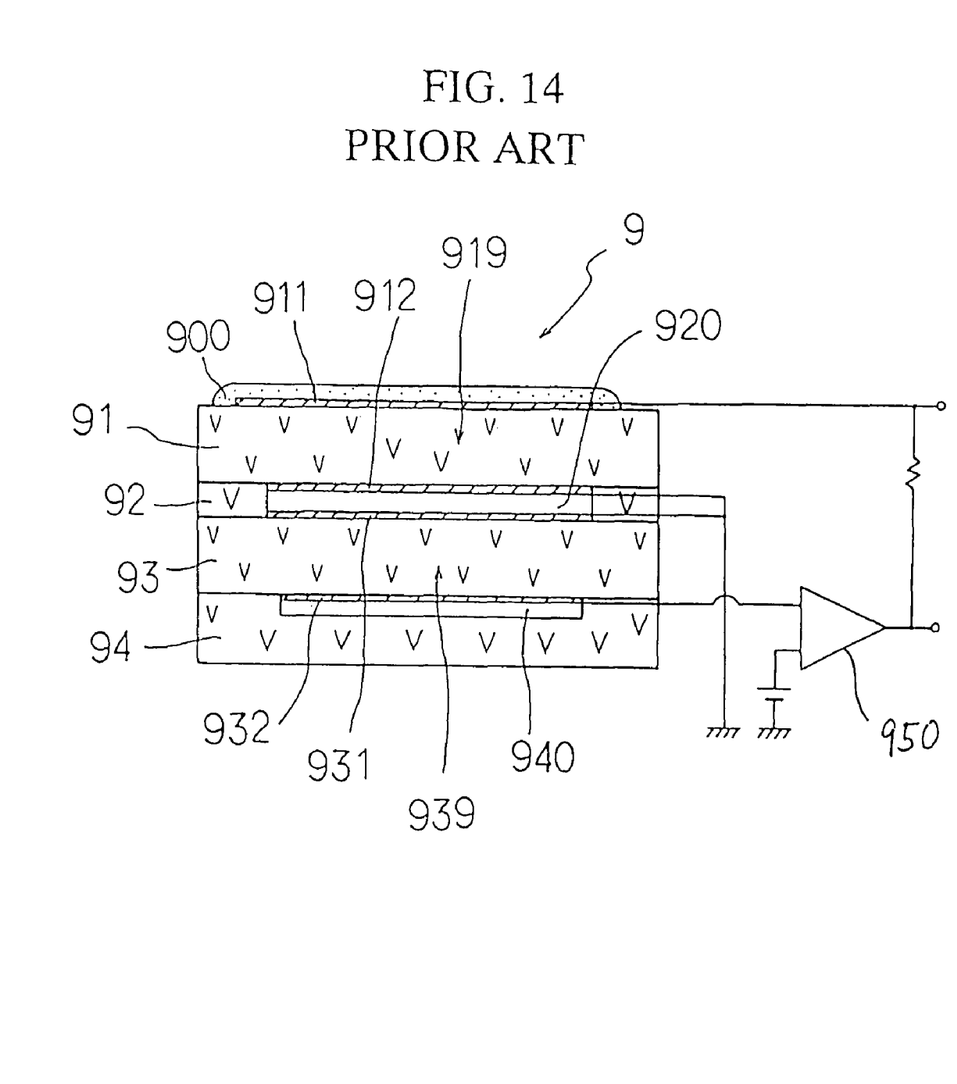
FIG. 14 is a cross-sectional view showing the conventional multilayered air-fuel ratio sensor shown in FIG. 13.

FIGS. 13 and 14 show a conventional multilayered air-fuel ratio sensor disclosed in Japanese Patent No. 2-62955 corresponding to U.S. Pat. No. 5,288,389.

As shown in FIG. 13, a multilayered air-fuel ratio sensor 9 comprises multiple layers consisting of a solid electrolytic substrate layer 91, an insulating spacer 92, a solid electrolytic substrate layer 93, and a shielding plate 94.

As shown in FIG. 14, the multilayered air-fuel ratio sensor 9 comprises a pump cell 919 and a sensor cell 939. A sample gas chamber 920 is interposed between the pump cells 919 and 939. A reference gas chamber 940 is provided between the sensor cell 939 and the shielding plate 94. Each of the solid electrolytic substrate layers 91 and 93 and the shielding plate 94 is made of zirconia. The insulating spacer 92 is made of alumina.

The pump cell 919 consists of the solid electrolytic substrate layer 91 and a pair of porous electrodes 911 and 912 provided on opposite surfaces of the solid electrolytic substrate layer 91. The sensor cell 939 consists of the solid electrolytic substrate layer 93 and a pair of electrodes 931 and 932 provided on opposite surfaces of the solid electrolytic substrate layer 91. A sample gas diffusive inlet portion 921 introduces a sample gas to the sample gas chamber 920. A protector layer 900 is provided on an outer surface of the porous electrode 911.

The pump cell 919 maintains the concentration of an oxygen gas residing in the sample gas chamber 920 at a constant value by adjusting an oxygen gas amount introduced to or exhausted from the sample gas chamber 920. The sensor cell 939 detects an air-fuel ratio of the sample gas stored in the sample gas chamber 920.

More specifically, a comparator 950 compares a sensing signal of the sensor cell 939 with a reference voltage. A voltage responsive to an output of the comparator 950 is applied to the pump cell 919. The oxygen gas amount varies in accordance with the applied voltage. Thus, an adjusted oxygen gas is introduced into or exhausted from the sample gas chamber 920. This realizes a feedback control of the concentration of the oxygen gas in the sample gas chamber 920. An obtained current during this feedback control is proportional to an air-fuel ratio of the sample gas. Thus, the air-fuel ratio is detectable from the measured current value.

In general, the air-fuel ratio sensor functions properly only when it has a high temperature exceeding a predetermined active temperature. Hence, to assure an accurate operation, the multilayered air-fuel ratio sensor 9 is equipped with a heater. The heater generates a sufficient amount of heat to maintain the multilayered air-fuel ratio sensor 9 at a higher temperature exceeding its active temperature.

The ULEV law, effective from the year of 2,000 in California State of the Unites States, forces the automotive makers to clear the required levels of tough emission controls. To attain this goal, having an excellent warmup ability is an essential factor to be realized for the above-described multilayered air-fuel ratio sensor.

The planned target levels are significantly high. For example, an air-fuel ratio sensor must operate properly within a short period of 5 seconds immediately after the engine is started up.

In this respect, the above-described conventional multilayered air-fuel ratio sensor 9 has a drawback in that its heater is provided as a separate component. According to this arrangement, the heater must increase its temperature excessively to satisfy the rough regulations. The multilayered air-fuel ratio sensor is subjected to severe thermal shocks. It possibly causes cracks.

As one of practical methods for reducing the thermal shocks, it may be possible to reduce an overall thickness of the multilayered air-fuel ratio sensor. A heat capacity of the multilayered air-fuel ratio sensor decreases in proportion to the reduction of its thickness. However, the mechanical strength of the multilayered air-fuel ratio sensor decreases correspondingly. This is not desirable.

The multilayered air-fuel ratio sensor usually receives various external forces and vibrations, for example, when the multilayered air-fuel ratio sensor is assembled with the heater or when the multilayered air-fuel ratio sensor is installed in an exhaust passage of an internal combustion engine. Accordingly, any multilayered air-fuel ratio sensor suffering from a decreased mechanical strength will be damaged by such external forces and vibrations.

Figure 15:
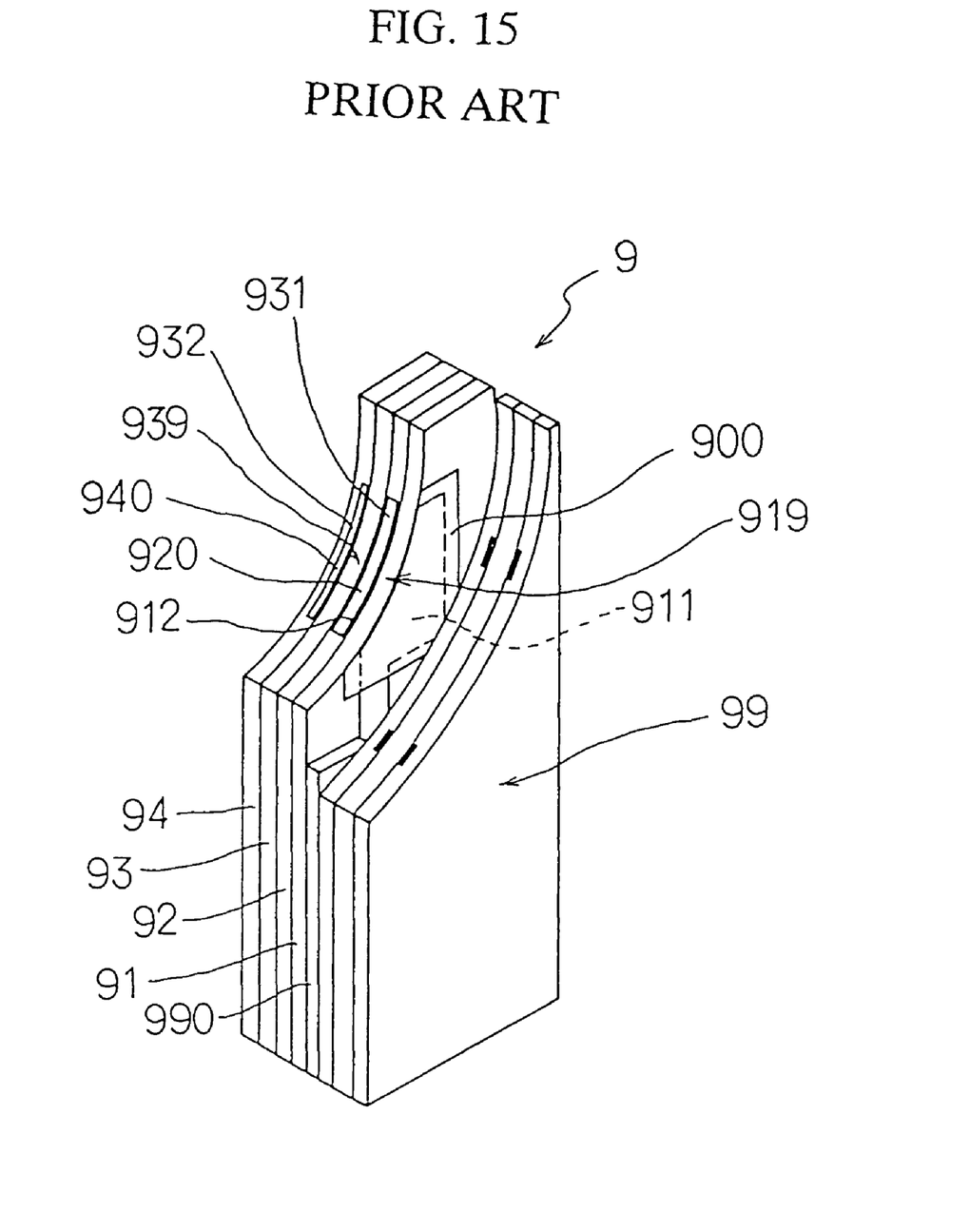
FIG. 15 is a perspective view showing an improved arrangement of the conventional multilayered air-fuel ratio sensor shown in FIG. 13.

FIG. 15 shows a proposed arrangement for the above conventional multilayered air-fuel ratio sensor 9. A multilayered heater 99 is integrated with the multilayered air-fuel ratio sensor 9 via an insulating substrate layer 990. However, according to this arrangement, the size of the multilayered air-fuel ratio sensor 9 is substantially restricted by the heat ability of the multilayered heater 99. As described above, increasing the heater temperature will cause the problem that the multilayered air-fuel ratio sensor 9 is subjected to severe thermal shocks. If the thickness of the multilayered air-fuel ratio sensor 9 is reduced to solve this problem, the mechanical strength will be fatally deteriorated.

SUMMARY OF THE INVENTION

In view of the problems encountered in the prior art, an object of the present invention is to provide a multilayered air-fuel ratio sensor having an excellent warmup ability and capable of effectively preventing the cracks from causing due to thermal shocks.

In order to accomplish this and other related objects, an aspect of the present invention provides a multilayered air-fuel ratio sensor comprising a plurality of substrate layers comprising at least one solid electrolytic substrate layer. At least one heterogeneous boundary layer is interposed between the plurality of substrate layers. The heterogeneous boundary layer has a thickness in a range of 10 to 100 µm. The heterogeneous boundary layer absorbs thermal shocks or any other stresses acting on the substrate layers and stops the growth of cracks.

Preferably, the heterogeneous boundary layer has a porosity larger than those of the neighboring substrate layers. The heterogeneous boundary layer has a sintering particle diameter larger than those of the neighboring substrate layers. The heterogeneous boundary layer comprises a component selected from the group consisting of alumina, spinel, and steatite. The heterogeneous boundary layer is interposed between a solid electrolytic substrate layer and an insulating substrate layer.

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF THE PREFERRED EMBODIMENTS

Preferred embodiments of the present invention will be explained hereinafter with reference to attached drawings. Identical parts are denoted by the same reference numerals throughout the views.

First Embodiment

FIGS. 1 through 8 are views showing preferable arrangements of a multilayered air-fuel ratio sensor 1 in accordance with a first embodiment of the present invention. In the following explanation, an up-and-down direction is defined based on the layout shown in FIG. 1. Needless to say, an actual up-and-down direction of the multilayered air-fuel ratio sensor 1 may be changed when it is installed on an internal combustion engine.

Figure 1:
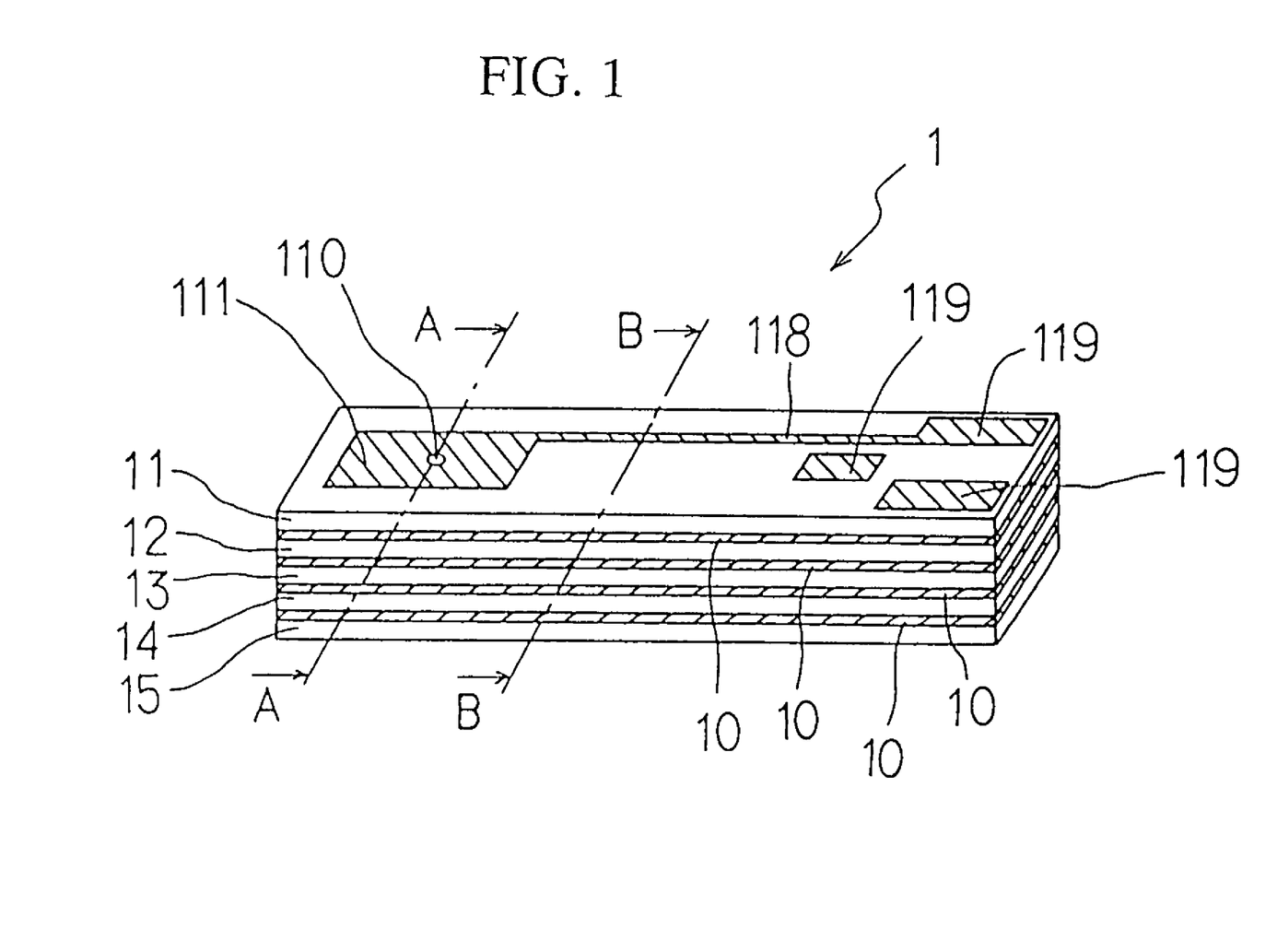
FIG. 1 is a perspective view showing an overall arrangement of a multilayered air-fuel ratio sensor in accordance with a first embodiment of the present invention.

The multilayered air-fuel ratio sensor 1 comprises a total of five solid electrolytic substrate layers 11 to 15, stacking from the bottom to the top in FIG. 1, each having the oxygen ion conductivity. A total of four heterogeneous layers 10 are alternately combined with the five solid electrolytic substrate layers 11 to 15. These heterogeneous layers 10 serve as boundary layers respectively interposed between two neighboring solid electrolytic substrate layers. Each heterogeneous layer 10 is 50 μm thick. Each of the solid electrolytic substrate layers 11 to 15 is 240 μm thick. A total thickness of the multilayered air-fuel ratio sensor 1 is 1.4 mm.

The solid electrolytic substrate layers 11 to 15 are made of yttria partially-stabilized zirconia with an average sintering particle diameter of 2 to 3 μm. Each heterogeneous layer 10 is made of a material selected from the group of alumina, spinel, and steatite. In this embodiment, the heterogeneous layers 10 are made of α-alumina with an average sintering particle diameter of 3 to 4 μm.

The multilayered air-fuel ratio sensor 1 comprises a pump cell and a sensor cell, as well as a multilayered heater integrally provided in the multilayered air-fuel ratio sensor 1.

Figure 2:
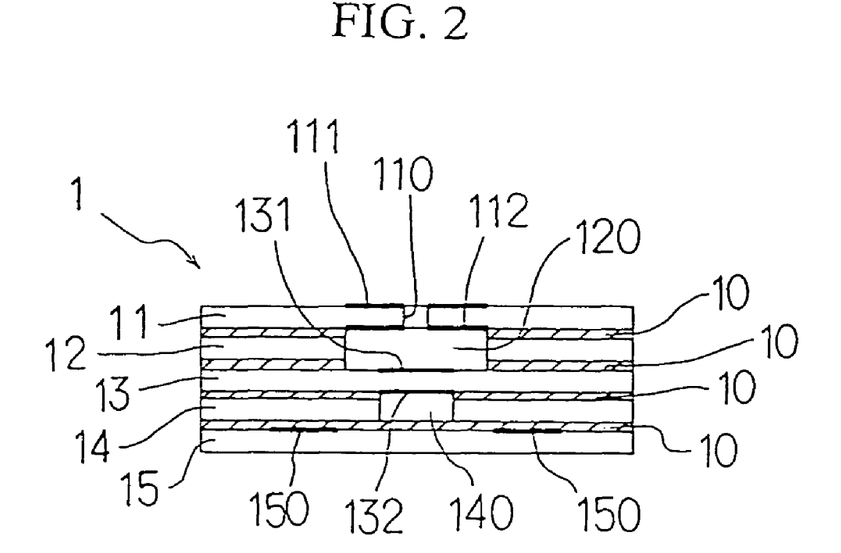
FIG. 2 is a cross-sectional view showing the multilayered air-fuel ratio sensor in accordance with the first embodiment of the present invention, taken along a line A-A of FIG. 1.
Figure 3:
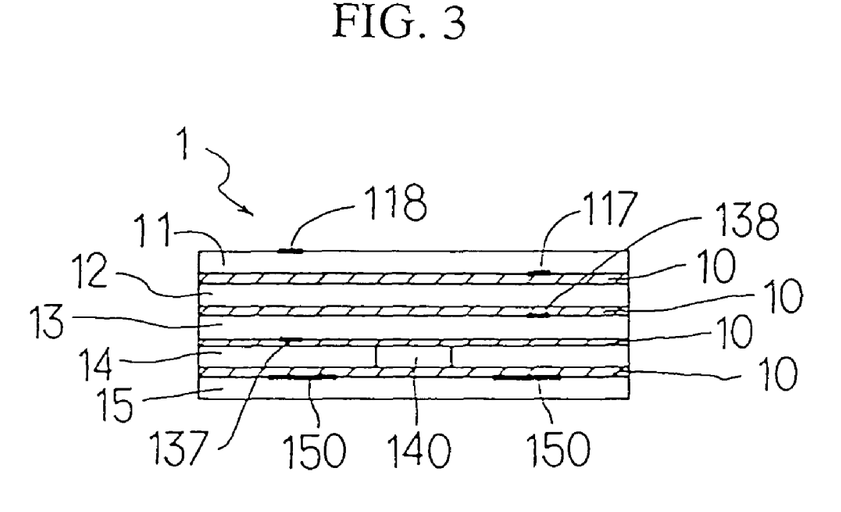
FIG. 3 is a cross-sectional view showing the multilayered air-fuel ratio sensor in accordance with the first embodiment of the present invention, taken along a line B-B of FIG. 1.

As shown in FIGS. 1 to 3, the solid electrolytic substrate layer 11 serves as a pump cell substrate having opposite surfaces on which pumping electrodes 111 and 112 are provided in a back-to-back relationship. A pinhole 110, serving as a sample gas introducing passage, extends across the solid electrolytic substrate layer 11 from a center of the upper (i.e., outer) pumping electrode 111 to a center of the lower (i.e., inner) pumping electrode 112.

The solid electrolytic substrate layer 12 has an aperture defining a sample gas chamber 120. A lower surface of the solid electrolytic substrate layer 11 defines a ceiling of the sample gas chamber 120. The lower pumping electrode 112 extends entirely along the ceiling of the sample gas chamber 120. The upper pumping electrode 111 extends along the upper surface of the solid electrolytic substrate layer 11.

An upper surface of the solid electrolytic substrate layer 13 defines a bottom of the sample gas chamber 120. The pinhole 110 communicated with the sample gas chamber 120.

The solid electrolytic substrate layer 13 serves as a sensor cell substrate having opposite surfaces on which sensing electrodes 131 and 132 are provided in a back-to-back relationship. The upper sensing electrode 131 extends along the bottom of the sample gas chamber 120.

The solid electrolytic substrate layer 14 has a slit defining a reference gas chamber 140. A lower surface of the solid electrolytic substrate layer 13 defines a ceiling of the reference gas chamber 140. The lower sensing electrode 132 extends entirely along the ceiling of the reference gas chamber 140. A bottom of the reference gas chamber 140 is defined by the heterogeneous layer 10 provided on an upper surface of the solid electrolytic substrate layer 15.

The solid electrolytic substrate layer 15 serves as a heater substrate. A heater element 150 is provided on the solid electrolytic substrate layer 15 via an insulation paste. The heater element 150 has a predetermined pattern extending along an upper surface of the solid electrolytic substrate layer 15.

In FIG. 3, reference numerals 117, 118, 137 and 138 denote leads connecting respective electrodes to corresponding output terminals. FIG. 1 shows an output terminal 119 connected via the lead 118 to the upper pumping electrode 111.

Next, a manufacturing procedure of the multilayered air-fuel ratio sensor 1 will be explained.

First, a manufacturing method of a zirconic green sheet is explained. The zirconic green sheet is used to form the solid electrolytic substrate layers 11 to 15. A main material of the zirconic green sheet is a yttria partially-stabilized zirconia with an average particle diameter of 0.5 μm. This yttria partially-stabilized zirconia comprises 6 mol % yttria and 94 mol % zirconia. The weighing capacity of the yttria partially-stabilized zirconia is 100 weight parts. As subsidiary materials of the zirconic green sheet, an α-alumina is one weight part, a PVB (polyvinyl butyral) is five weight parts, a DBP (di-butyl phthalate) is 10 weight parts, an ethanol is 10 weight parts, and a toluene is 10 weight parts.

The prepared yttria partially-stabilized zirconia, α-alumina, PVB, DBP, ethanol and toluene are mixed in a ball mill to obtain a slurry of them. The obtained slurry is configured into a plane sheet body by using a doctor blade method. The fabricated sheet body is 0.3 mm thick in a dried condition. A total of five rectangular sheet bodies, each being 5 mm×70 mm, are cut out of this sheet body for the solid electrolytic substrate layers 11 to 15.

Next, an electrically conductive Pt paste is screen printed in the predetermined pattern on opposite surfaces of a first rectangular sheet body. This constructs the solid electrolytic substrate layer (i.e., sensor cell substrate) with the sensing electrodes 131 and 132.

In the same manner, the electrically conductive Pt paste is screen printed on opposite surfaces of a second rectangular sheet body. This constructs the solid electrolytic substrate layer (i.e., pump cell substrate) 11 with the pumping electrodes 111 and 112. The pinhole 11 is opened across the solid electrolytic substrate layer 11. The diameter of the opened pinhole 11 is 0.5 mm.

Furthermore, the leads and the output terminals are provided at the predetermined portions on the first and second rectangular sheet bodies of the sensor cell substrate 13 and the pump cell substrate 11.

Furthermore, an alumina insulating paste is printed on a third rectangular sheet body. Thereafter, an electrically conductive paste containing 90 wt % Pt and 10 wt % aluminum is printed on this third rectangular sheet body. This constructs the solid electrolytic substrate layer (i.e., heater substrate) 15 with the heater element 150. The resistance value of the formed heater element 150 is 2.0Ω at 20° C.

Furthermore, a fourth rectangular sheet body is provided with an aperture at a predetermined position. This constructs the solid electrolytic substrate layer 12 defining the sample gas chamber 120. A fifth rectangular sheet body is provided with a slit at a predetermined position. This constructs the solid electrolytic substrate layer 14 defining the reference gas chamber 140.

Next, a manufacturing method of an alumina green sheet will be explained. The alumina green sheet is used to form the heterogeneous layers 10. A main material of the aluminum green sheet is an α-alumina with an average particle diameter of 0.3 μm. The weighing capacity of this α-alumina is 100 weight parts. As subsidiary materials (i.e., binders), an acrylic resin is 30 weight parts and a toluene is 30 weight parts.

The prepared α-alumina, acrylic resin and toluene are kneaded by a roll mill to get a predetermined viscosity and then sheeted by a press roller. The fabricated sheet body is 100 μm thick. A total of four rectangular sheet bodies, each being 5 mm×70 mm, are cut out of this plane sheet body for the heterogeneous layers 10. The rectangular sheet bodies are configured into the predetermined shape corresponding to the above-described pinhole 110 and the gas chambers 120 and 140.

Subsequently, the rectangular sheet bodies of the solid electrolytic substrate layers 11 to 15 are stacked or laminated in the predetermined order with the alternately intervening rectangular sheet bodies of the heterogeneous layers 10, as shown in FIGS. 1 to 3. Then, the formed multilayered assembly is sintered at an atmospheric environment of 1,500° C. for one hour. Finishing this sintering operation obtains the multilayered air-fuel ratio sensor of this embodiment.

Next, the performance of the multilayered air-fuel ratio sensor of this embodiment will be explained.

To check the performance, the multilayered air-fuel ratio sensor of the first embodiment was compared with several test samples. In the conducted comparative performance test, a plurality of green sheets respectively 0.35, 0.33, 0.25 and 0.21 mm thick were prepared for the solid electrolytic substrate. Similarly, a plurality of green sheets respectively 0 (i.e., none), 40, 200 and 280 μm thick were prepared for the heterogeneous layers. By appropriately assembling the prepared green sheets, various test samples of the multilayered air-fuel ratio sensor were obtained. Each test sample was sintered. Each obtained air-fuel ratio sensor was approximately 1.4 mm thick after finishing the sintering operation. This thickness is substantially the same as that of the multilayered air-fuel ratio sensor of the above-described embodiment.

Figure 4:
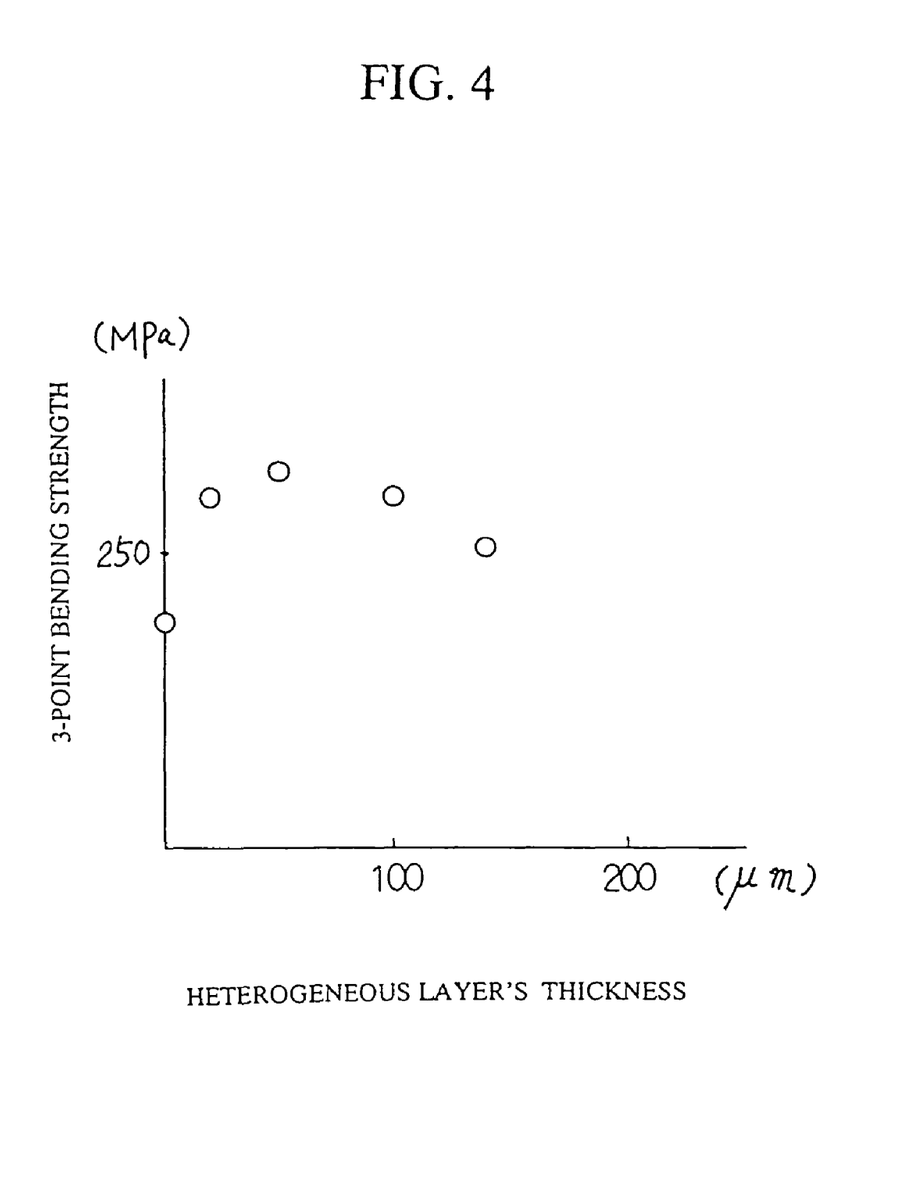
FIG. 4 is a graph showing a relationship between the thickness of a heterogeneous layer and the bending strength of the multilayered air-fuel ratio sensor in accordance with the first embodiment of the present invention.
Figure 5:
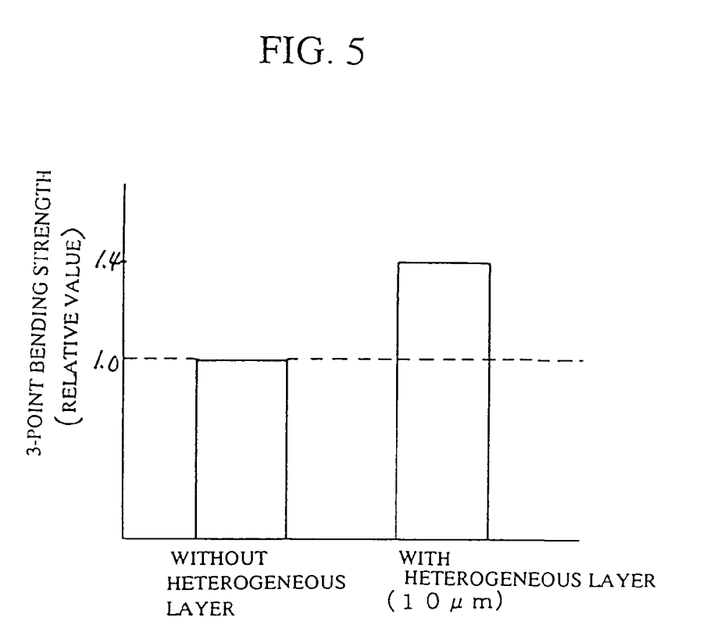
FIG. 5 is a graph showing a relationship between the presence of the heterogeneous layer and the bending strength of the multilayered air-fuel ratio sensor in accordance with the first embodiment of the present invention.

The thickness dispersion of each test sample was suppressed within 50 μm. The thickness of each heterogeneous layer was measured through a SEM observation on a broken surface. The measured thicknesses of the heterogeneous layers were 0, 20, 50, 100 and 140 μm after finishing the sintering operation. In each of the five kinds of test samples, a 3-point bending strength was measured in compliance with JISB0601. FIGS. 4 and 5 show the measured result.

According to the measured result of FIG. 4, the 3-point bending strength is larger than 250 MPa when the thickness of the heterogeneous layer is in a range of 10 μm to 100 μm. The mechanical strength is practically sufficient when the 3-point bending strength exceeds 250 Mpa.

According to the measured result of FIG. 5, the tested air-fuel sample with a 10 μm heterogeneous layer shows an increased 3-point bending strength that is approximately 1.4 times as large as that of the tested air-fuel sample having no heterogeneous layer.

As shown in FIG. 4, the 3-point bending strength is maximized in the vicinity of 50 μm. In other words, the optimum thickness of the heterogeneous layer resides near 50 μm.

Figure 6:
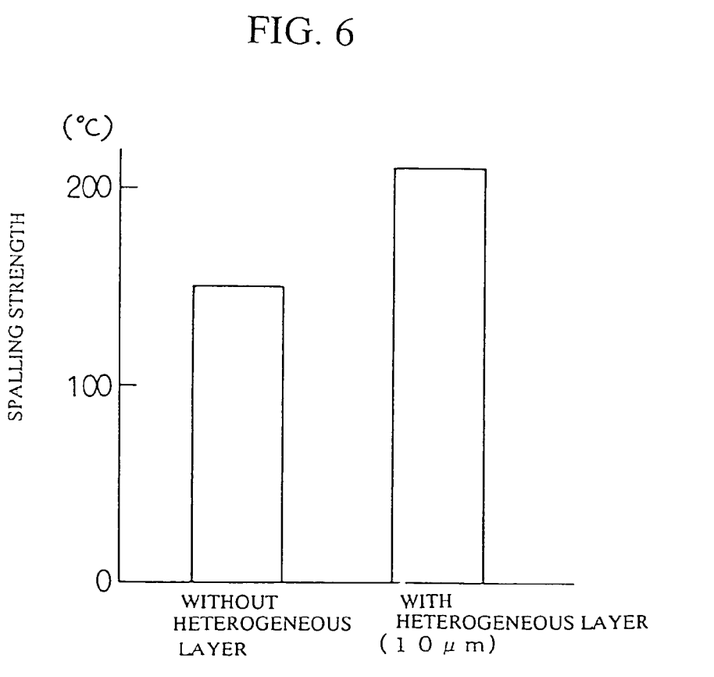
FIG. 6 is a graph showing a relationship between the presence of the heterogeneous layer and the breaking strength of the multilayered air-fuel ratio sensor in accordance with the first embodiment of the present invention.

FIG. 6 shows a result of a spalling strength test. This shows a relationship between the presence of the heterogeneous layer and the breaking strength of the multilayered air-fuel ratio sensor. To measure the breaking strength, the test samples were held in a dried environment of a predetermined temperature for 30 minutes and then soaked in water.

As apparent from the graph of FIG. 6, a large thermal shock durability (temperature difference) is obtained by providing the heterogeneous layer in the multilayered air-fuel ratio sensor. It is thus confirmed that the breaking strength can be improved by providing the heterogeneous layer. The air-fuel ratio sensor is installed in an exhaust pipe of an internal combustion engine. The air-fuel ratio sensor in an engine startup condition is usually subjected to condensed water remaining in the exhaust pipe. However, in such a severe condition, the present invention can effectively prevent the multilayered air-fuel ratio sensor from causing a thermal stress cracking by the provision of the heterogeneous layer.

Next, functions and effects of the above-described embodiment of the present invention will be explained.

According to the first embodiment, the multilayered air-fuel ratio sensor 1 has heterogeneous layers 10 each serving as a boundary layer interposed between two neighboring solid electrolytic substrate layers. When a thermal stress or any other stress acts on the solid electrolytic substrate layers 11~15, a small crack may appear. However, the heterogeneous layer acts as a buffer for absorbing the stresses. The growth of the crack is surely prevented by the heterogeneous layer. Thus, the multilayered air-fuel ratio sensor 1 is free from the fatal cracking.

Thus, the first embodiment of the present invention can provide a multilayered air-fuel ratio sensor robust against thermal shocks. This allows an increased heater temperature. Needless to say, increasing the heater temperature is effective to improve the warmup ability. Accordingly, the first embodiment of the present invention provides a multilayered air-fuel ratio sensor having an excellent warmup ability.

According to the first embodiment, the solid electrolytic substrate layers 11~15 are made of yttria partially-stabilized zirconia. The heterogeneous layer 10 is made of alumina. The thermal expansion coefficient of the yttria partially-stabilized zirconia is substantially the same as that of the alumina. No damage occurs due to a thermal expansion coefficient difference between the yttria partially-stabilized zirconia and the alumina.

As described above, the first embodiment of the present invention provides the multilayered air-fuel ratio sensor excellent in the warmup ability and robust against the thermal shocks.

Figure 7:
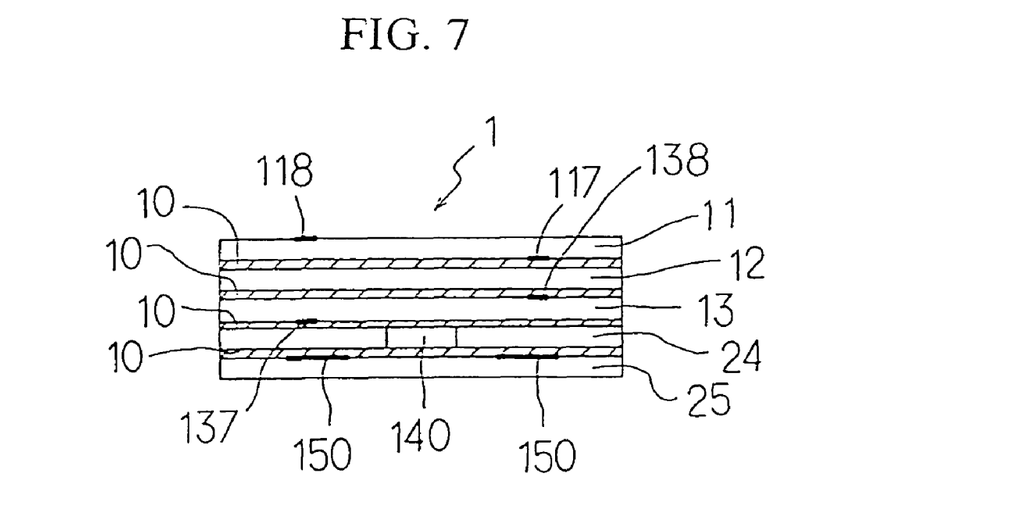
FIG. 7 is a cross-sectional view showing an essential arrangement of a multilayered air-fuel ratio sensor having two insulating substrate layers in accordance with the first embodiment of the present invention.

FIG. 7 shows a modified arrangement of the multilayered air-fuel ratio sensor of the first embodiment wherein two solid electrolytic substrate layers 14 and 15 are replaced by insulating substrate layers 24 and 25. More specifically, the multilayered air-fuel ratio sensor 1 shown in FIG. 7 comprises three solid electrolytic substrate layers 11~13 and two insulating substrate layers 24 and 25 stacked to form a multilayered construction. The insulating substrate layers 24 and 25 are made of alumina. A total of four heterogeneous layers 10 are alternately combined with the five substrate layers 11~13 and 24~25. These heterogeneous layers 10 serve as boundary layers respectively interposed between two neighboring substrate layers for absorbing the stresses.

Figure 8:
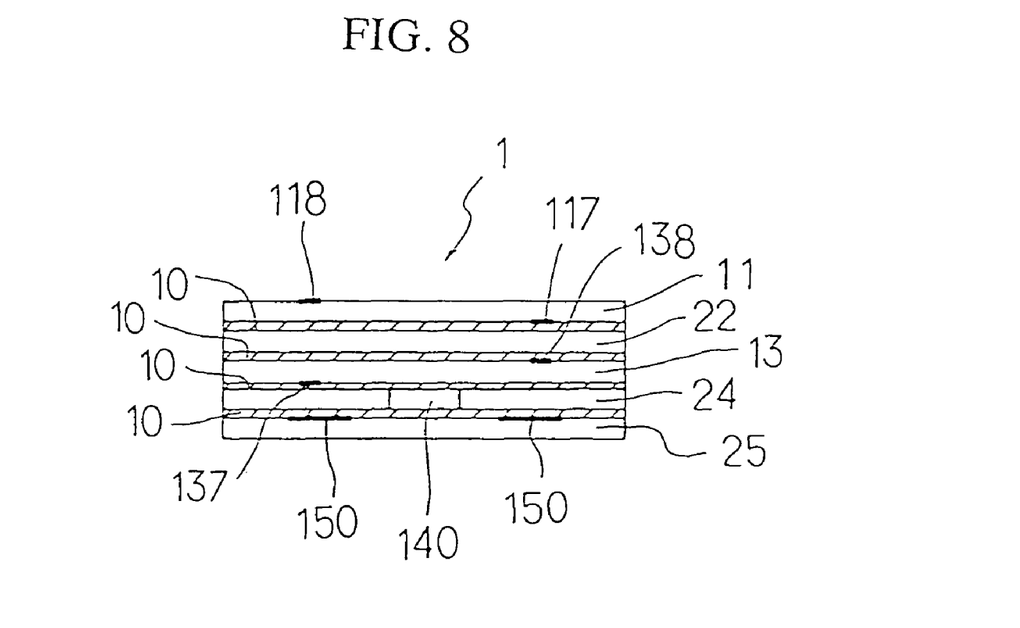
FIG. 8 is a cross-sectional view showing an essential arrangement of a multilayered air-fuel ratio sensor having three insulating substrate layers in accordance with the first embodiment of the present invention.

FIG. 8 shows another modified arrangement of the multilayered air-fuel ratio sensor of the first embodiment wherein three solid electrolytic substrate layers 12, 14 and 15 are replaced by insulating substrate layers 22, 24 and 25.

Both of the modified arrangements shown in FIGS. 7 and 8 bring substantially the same functions and effects as those of the above-described FIGS. 1~3 embodiment.

As apparent from the foregoing description, the present invention provides the multilayered air-fuel ratio sensor comprising a plurality of substrate layers comprising at least one solid electrolytic substrate layer. At least one heterogeneous layer is interposed between two of the plurality of substrate layers. The heterogeneous layer serves as a boundary layer that absorbs thermal shocks or any other stresses acting on the substrate layers and stops the growth of cracks.

The heterogeneous layer has a thickness in a range of 10 to 100 μm. When the thickness of the heterogeneous layer is smaller than 10 μm, the effects of the present invention may not be obtained. When the thickness of the heterogeneous layer is larger than 100 μm, the heterogeneous layer may behave as a bulk body that is weak against thermal shocks. The cracks may be generated. Furthermore, the thickness of the sensor increases. This deteriorates the warmup ability.

Preferably, the heterogeneous layers are provided at all of boundaries of the substrate layers. However, the effect of the present invention can be obtained by providing at least one heterogeneous layer.

Preferably, the heterogeneous layer has a porosity larger than those of the neighboring substrate layers. When the porosity is large, the buffer effect of the heterogeneous layer can be enhanced.

Preferably, the heterogeneous layer has a sintering particle diameter larger than those of the neighboring substrate layers. When the sintering particle diameter is large, the buffer effect of the heterogeneous layer can be enhanced.

Preferably, the heterogeneous layer comprises a component selected from the group consisting of alumina, spinel, and steatite. These materials are insulating materials capable of serving as an insulating substrate layer. The thermal expansion coefficients of these materials are substantially the same as that of the solid electrolytic substrate layer. No damage occurs due to a thermal expansion coefficient difference between the heterogeneous layer and the slid electrolytic substrate layer.

When the solid electrolytic substrate layer is made of a zirconic material, it is preferable to use a heterogeneous layer made of alumina in view of the insulation ability and the thermal expansion coefficient. A sintering operation produces a thermal expansion coefficient difference due to a thermal hysteresis. The combination of the zirconic material and the alumina material is preferable to suppress a stress caused by such a thermal expansion coefficient difference.

Preferably, the heterogeneous layer is interposed between a solid electrolytic substrate layer and an insulating substrate layer.

Preferably, the multilayered air-fuel ratio sensor comprises a multilayered heater.

Second Embodiment

Figure 9:
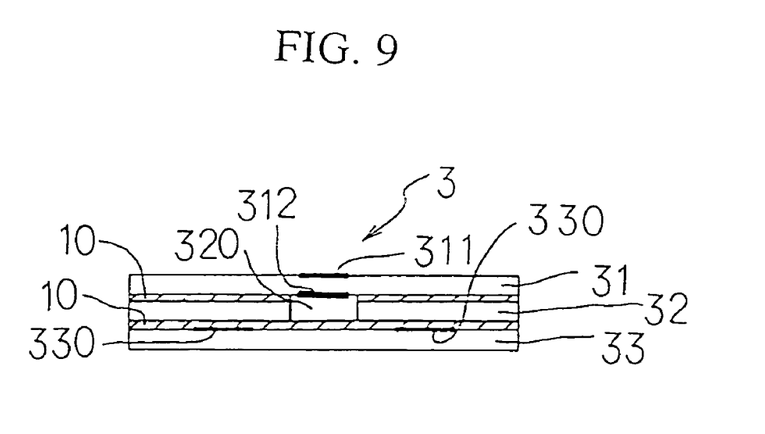
FIG. 9 is a cross-sectional view showing an essential arrangement of a multilayered air-fuel ratio sensor having three solid electrolytic substrate layers in accordance with a second embodiment of the present invention.
Figure 10:
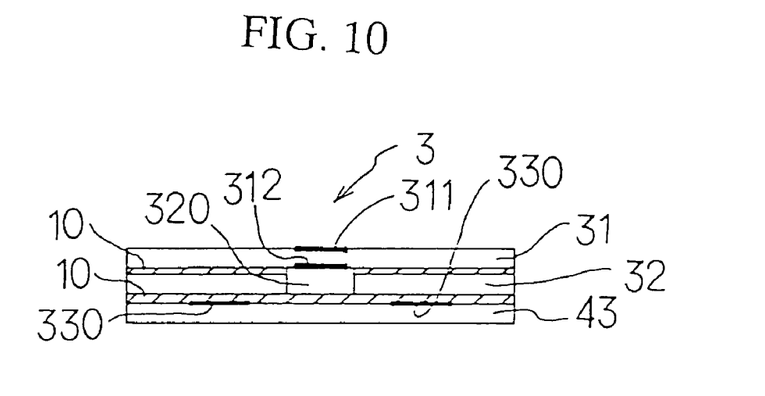
FIG. 10 is a cross-sectional view showing an essential arrangement of a multilayered air-fuel ratio sensor having one insulating substrate layer in accordance with the second embodiment of the present invention.
Figure 11:
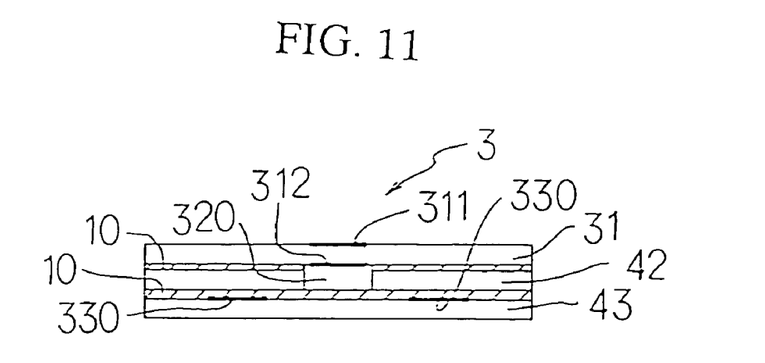
FIG. 11 is a cross-sectional view showing an essential arrangement of a multilayered air-fuel ratio sensor having two insulating substrate layers in accordance with the second embodiment of the present invention.

FIGS. 9 through 11 are views showing preferable arrangements of a multilayered air-fuel ratio sensor 3 in accordance with a second embodiment of the present invention. The multilayered air-fuel ratio sensor 3 comprises a total of three substrate layers.

According to an arrangement shown in FIG. 9, the multilayered air-fuel ratio sensor 3 comprises an upper solid electrolytic substrate layer 31 with upper and lower electrodes 311 and 312 provided on opposed surfaces thereof in a back-and-back relationship. A medium solid electrolytic substrate layer 32 is provided with a slit defining a reference gas chamber 320. A lower surface of the upper solid electrolytic substrate layer 31 defines a ceiling of the reference gas chamber 320. The lower electrode 312 extends entirely along the ceiling of the reference gas chamber 320.

A bottom of the reference gas chamber 320 is defined by an upper surface of a heterogeneous layer 10 mounted on a lower solid electrolytic substrate layer 33. The lower solid electrolytic substrate layer 33 serves as a heater substrate on an upper surface of which a heater element 330 is provided via an insulating paste layer. Another heterogeneous layer 10 is interposed between the upper and medium solid electrolytic substrate layers 31 and 32.

FIG. 10 shows another arrangement of the multilayered air-fuel ratio sensor 3 of the second embodiment wherein the lower solid electrolytic substrate layers 33 is replaced by an insulating substrate layer 43.

FIG. 11 shows another arrangement of the multilayered air-fuel ratio sensor 3 of the second embodiment wherein both of the medium and lower solid electrolytic substrate layers 32 and 33 are replaced by insulating substrate layer 42 and 43.

Both of the modified arrangements shown in FIGS. 10 and 11 bring substantially the same functions and effects as those of the above-described FIG. 9 embodiment.

Third Embodiment

Figure 12:
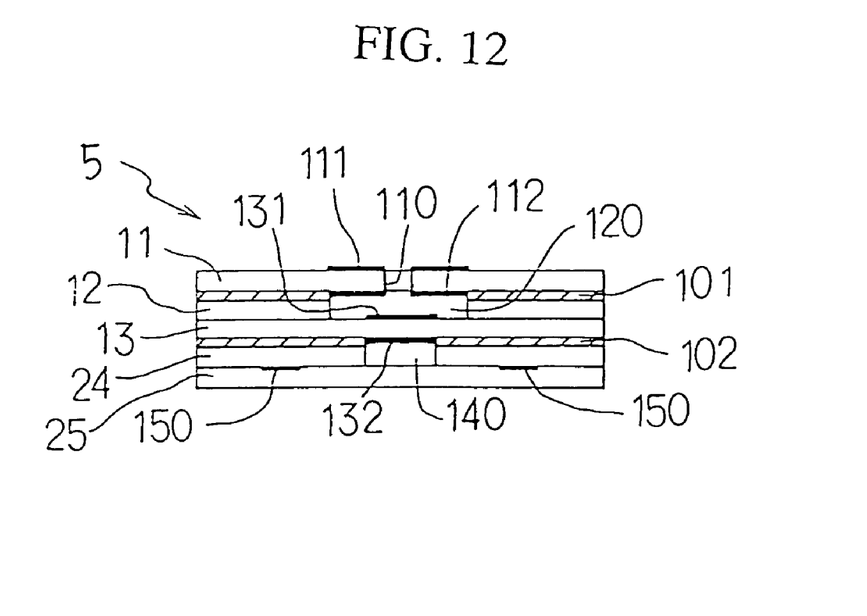
FIG. 12 is a cross-sectional view showing an essential arrangement of a multilayered air-fuel ratio sensor having two heterogeneous layers in accordance with a third embodiment of the present invention.

FIG. 12 is a view showing a preferable arrangement of a multilayered air-fuel ratio sensor 5 in accordance with a third embodiment. The multilayered air-fuel ratio sensor 5 comprises three solid electrolytic substrate layers 11~13 and two insulating substrate layers 24~25. One heterogeneous layer 101 is interposed between the solid electrolytic substrate layers 11 and 12. Another heterogeneous layer 102 is interposed between the solid electrolytic substrate layer 13 and the insulating substrate layer 24. Both of the heterogeneous layers 101 and 102 are insulating layers made of alumina.

According to the arrangement of the third embodiment, the heterogeneous layer 101 has a function of insulating the solid electrolytic substrate layer 11 from the solid electrolytic substrate layer 12 or vice versa as well as a function of absorbing the thermal shocks.

The FIG. 12 embodiment brings substantially the same functions and effects as those of the above-described first embodiment.

This invention may be embodied in several forms without departing from the spirit of essential characteristics thereof. The present embodiments as described are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A multilayered air-fuel ratio sensor having a plurality of stacked layers comprising:
   a plurality of substrate layers comprising at least one solid electrolytic substrate layer and at least one insulating substrate layer; and
   a boundary layer interposed immediately between said solid electrolytic substrate layer and said insulating substrate layer without any other intervening layer;
   wherein each of said solid electrolytic substrate layer, said insulating substrate layer, and said boundary layer is obtained by sintering original particles of a source material so as to change the original particles to sintered particles, and an average size of the sintered particles of said boundary layer is adjusted to be larger than an average size of the sintered particles of each of said solid electrolytic substrate layer and said insulating substrate layer,
   wherein said boundary layer comprises a component selected from the group consisting of alumina, spinel, and steatite, and
   wherein said boundary layer is made primarily from α-alumina with an average sintering particle diameter of 3 to 4 μm.

2. The multilayered air-fuel ratio sensor according to claim 1, wherein said boundary layer has a porosity larger than that of said substrate layers.

3. The multilayered air-fuel ratio sensor according to claim 1, wherein said boundary layer has a thickness in a range of 10 to 100 μm.

4. The multilayered air-fuel ratio sensor according to claim 1, wherein said substrate layers comprise a plurality of solid electrolytic substrate layers, and further comprising a plurality of additional boundary layers, respectively interposed immediately between two consecutive solid electrolytic substrate layers without any other intervening layer.

5. The multilayered air-fuel ratio sensor according to claim 1, wherein the composition of said boundary layer is different from the composition of said solid electrolytic substrate layer.

6. The multilayered air-fuel ratio sensor according to claim 5, wherein the composition of said boundary layer is different from the composition of said insulating substrate layer.

7. The multilayered air-fuel ratio sensor according to claim 5, wherein said insulating substrate layer is made of alumina.

8. The multilayered air-fuel ratio sensor according to claim 1, wherein said at least one solid electrolytic substrate layer is made of yttria partially-stabilized zirconia with an average sintered particle diameter of 2 to 3 μm.

9. The multilayered air-fuel ratio sensor according to claim 1, wherein said insulating substrate layer is formed from a component selected from the group consisting of alumina, spinel and steatite.

10. The multilayered air-fuel ratio sensor according to claim 1, wherein said insulating substrate layer is made of alumina.

11. The multilayered air-fuel ratio sensor according to claim 1, wherein an average size of the original particles of said boundary layer is smaller than an average size of the original particles of each of said substrate layers.

12. A multilayered air-fuel ratio sensor having a plurality of stacked layers comprising:
    a plurality of substrate layers comprising at least one solid electrolyte substrate layer and at least one insulating substrate layer; and
    a boundary layer interposed immediately between said solid electrolytic substrate layer and said insulating substrate layer without any other intervening layer;
    wherein each of said solid electrolyte substrate layer, said insulating substrate layer, and said boundary layer is obtained by sintering original particles of a source material so as to change the original particles to sintered particles, and an average size of the sintered particles of said boundary layer is adjusted to be larger than an average size of the sintered particles of each of said solid electrolytic substrate layer and said insulating substrate layer and wherein the composition of said boundary layer is different from the composition of said solid electrolytic substrate layer,
    wherein said boundary layer comprises a component selected from the group consisting of alumina, spinel, and steatite, and wherein said boundary layer is made primarily from α-alumina with an average sintered particle diameter of 3 to 4 μm.

13. The multilayered air-fuel ratio sensor according to claim 12, wherein said boundary layer has a porosity that is larger than that of said substrate layers.

14. The multilayered air-fuel ratio sensor according to claim 12, wherein said boundary layer has a thickness that is in the range of 10 to 100 μm.

15. The multilayered air-fuel ratio sensor according to claim 12, wherein said substrate layers comprise a plurality of solid electrolytic substrate layers, and further comprising a plurality of additional boundary layers, respectively interposed immediately between two consecutive solid electrolytic substrate layers without any other intervening layer.

16. The multilayered air-fuel ratio sensor according to claim 12, wherein said at least one solid electrolytic substrate layer is made of yttria partially-stabilized zirconia with an average sintered particle diameter of 2 to 3 μm.

17. The multilayered air-fuel ratio sensor according to claim 12, wherein said insulating substrate layer is formed from a component selected from the group consisting of alumina, spinel and steatite.

18. The multilayered air-fuel ratio sensor according to claim 12, wherein said insulating substrate layer is made of alumina.

19. The multilayered air-fuel ratio sensor according to claim 12, wherein an average size of the original particles of said boundary layer is smaller than an average size of the original particles of each of said substrate layers.

20. A multilayered air-fuel ratio sensor having a plurality of stacked layers comprising:
a plurality of substrate layers comprising one solid electrolytic substrate layer serving as a ceiling or a bottom of a sample gas chamber into which a sample gas is introduced and another solid electrolytic substrate layer defining side walls of said sample gas chamber; and
a boundary layer interposed immediately between said one solid electrolytic substrate layer and said another solid electrolytic substrate layer without any other intervening layer;
wherein each of said one solid electrolytic substrate layer, said another solid electrolytic substrate layer, and said boundary layer is obtained by sintering original particles of a source material so as to change the original particles to sintered particles, and an average size of the sintered particles of said boundary layer is adjusted to be larger than an average size of the sintered particles of each of said solid electrolytic substrate layers, and
wherein said boundary layer is made of α-alumina with an average sintered particle size of 3 to 4 μm.

21. The multilayered air-fuel ratio sensor in accordance with claim 20, wherein
said solid electrolytic substrate layers are made of partially-stabilized zirconia with an average sintered particle size of 2 to 3 μm.

22. The multilayered air-fuel ratio sensor in accordance with claim 21, wherein
an alumina green sheet for said boundary layer has an average particle diameter smaller than that of a zirconic green sheet for said solid electrolytic substrate layers.

23. The multilayered air-fuel ratio sensor in accordance with claim 20, wherein said solid electrolytic substrate layers are made of partially-stabilized zirconia and said boundary layer is made of alumina, and
a thermal expansion coefficient of said partially-stabilized zirconia is substantially the same as that of said alumina.

24. The multilayered air-fuel ratio sensor according to claim 20, wherein said boundary layer has a thickness in a range of 10 to 100 μm.

25. The multilayered air-fuel ratio sensor according to claim 20, wherein an average size of the original particles of said boundary layer is smaller than an average size of the original particles of each of said substrate layers.

26. A multilayered air-fuel ratio sensor having a plurality of stacked layers comprising:
a plurality of substrate layers comprising one solid electrolytic substrate layer serving as a ceiling or a bottom of a sample gas chamber into which a sample gas is introduced and another solid electrolytic substrate layer defining side walls of said sample gas chamber; and
a boundary layer interposed immediately between said one solid electrolytic substrate layer and said another solid electrolytic substrate layer without any other intervening layer;
wherein each of said one solid electrolytic substrate layer, said another solid electrolytic substrate layer, and said boundary layer is obtained by sintering original particles of a source material so as to change the original particles to sintered particles, and an average size of the sintered particles of said boundary layer is adjusted to be larger than an average particle size of the sintered particles of said solid electrolytic substrate layers, and wherein the composition of said boundary layer is different from the composition of each of said solid electrolytic substrate layers, and
wherein said boundary layer is made of α-alumina with an average sintered particle size of 3 to 4 μm.

27. The multilayered air-fuel ratio sensor in accordance with claim 26, wherein
said solid electrolytic substrate layers are made of partially-stabilized zirconia with an average sintered particle size of 2 to 3 μm.

28. The multilayered air-fuel ratio sensor in accordance with claim 27, wherein
an alumina green sheet for said boundary layer has an average particle diameter smaller than that of a zirconic green sheet for said solid electrolytic substrate layers.

29. The multilayered air-fuel ratio sensor in accordance with claim 26, wherein
said solid electrolytic substrate layers are made of partially-stabilized zirconia and said boundary layer is made of alumina, and
a thermal expansion coefficient of said partially-stabilized zirconia is substantially the same as that of said alumina.

30. The multilayered air-fuel ratio sensor according to claim 26, wherein said boundary layer has a thickness in a range of 10 to 100 μm.

31. The multilayered air-fuel ratio sensor according to claim 26, wherein an average size of the original particles of said boundary layer is smaller than an average size of the original particles of each of said substrate layers.

* * * * *